(12) United States Patent
Garrait et al.

(10) Patent No.: US 6,479,695 B1
(45) Date of Patent: Nov. 12, 2002

(54) PROCESS FOR THE PREPARATION OF HYDROXY METHYLTHIOBUTYRIC ACID ESTERS

(75) Inventors: Michel Garrait, Millery (FR); Claude Casse, Decines-Charpieu (FR); Georges Gros, Antony (FR)

(73) Assignee: Aventis Animal Nutrition, S.A., Antony (FR)

( * ) Notice: Subject to any disclaimer, the term of this patent is extended or adjusted under 35 U.S.C. 154(b) by 0 days.

(21) Appl. No.: 09/937,702

(22) PCT Filed: Mar. 30, 2000

(86) PCT No.: PCT/EP00/03101

§ 371 (c)(1),
(2), (4) Date: Dec. 28, 2001

(87) PCT Pub. No.: WO00/59877

PCT Pub. Date: Oct. 12, 2000

(30) Foreign Application Priority Data

Apr. 2, 1999 (FR) .............................................. 99/04142

(51) Int. Cl.⁷ ..................... C07C 321/00; C07C 323/00; C07C 381/00; A23L 383/00

(52) U.S. Cl. ........................... 560/152; 426/2; 562/581; 564/129

(58) Field of Search ........................ 560/152; 562/581; 426/2; 564/129

(56) References Cited

U.S. PATENT DOCUMENTS 2,745,745 A * 5/1956 Blake et al. ...................... 99/4
2,938,053 A * 5/1960 Blake et al. .................. 260/561
4,000,318 A * 12/1976 Ferguson et al. .............. 426/2
4,524,077 A 6/1985 Ruest et al. ................. 514/557

FOREIGN PATENT DOCUMENTS

| AU | 478542 | * | 3/1973 |
| DE | 1 063 443 | * | 9/1958 |
| EP | 0 601 195 | | 6/1994 |
| GB | 2 044 755 A | * | 10/1980 |

OTHER PUBLICATIONS

M. Kazuyuki, "Production of 2–Hydroxymethylmercaptobutyric acid". Patent Abstracts of Japan of JP 08157447, published Jun. 18, 1996.

W.J. Greenlee et al., "Mild Conversion of Carboxamides and Carboxylic Acid Hydrazides to Acids and Esters", Journal of Organic Chemistry, vol. 46, No. 25, Dec. 4, 1981, pp. 5351–5353, XP002124735.

P.L. Anelli et al., "Mile Conversion of Primary Carboxamides Into Carboxylic Esters", Tetrahedron Letters, vol. 38, No. 13, Mar. 31, 1997, pp. 2367–2368, XP004056673.

* cited by examiner

Primary Examiner—Mukund J. Shah
Assistant Examiner—Zachary C. Tucker
(74) Attorney, Agent, or Firm—Finnegan, Henderson, Farabow, Garrett & Dunner, L.L.P.

(57) ABSTRACT

A process for the preparation of 2-hydroxy-4-methylthiobutyric acid ester which comprises (a) a first step of reacting 2-hydroxy-4-methylthiobutyronitrile with sulphuric acid to produce 2-hydroxy-4-methylthiobutyramide, and (b) a second step of reacting the 2-hydroxy-4-methylthiobutyramide with an alcohol to produce a 2-hydroxy-4-methylthiobutyric acid ester, the two steps being carried out in the same reaction medium.

13 Claims, No Drawings

PROCESS FOR THE PREPARATION OF HYDROXY METHYLTHIOBUTYRIC ACID ESTERS

This application is a national stage filing of PCT International Application No. PCT/EP00/03101, filed on Mar. 30, 2000. This application also claims the benefit of priority under 35 U.S.C. §119(a) to French patent application no. 99/04142, filed on Apr. 2, 1999.

The present invention relates to a process for the preparation of 2-hydroxy-4-methylthiobutyric acid esters and in particular to a two-stage process consisting of hydrating 2-hydroxy-4-methylthiobutyronitrile and then esterifying the intermediate product obtained.

2-Hydroxy-4-methylthiobutyric acid is known to be used as a methionine analogue for feeding breeding animals and mainly, among these animals, poultry. This product is marketed under the trademarks Rhodimet AT 88™ or Alimet™.

It is known to prepare 2-hydroxy-4-methylthiobutyric acid by various processes for hydrating 2-hydroxy-4-methylthiobutyronitrile. The hydrolysis is carried out with an inorganic acid such as hydrochloric or sulphuric acid or it can also be carried out by enzymatic hydrolysis.

The esters have been prepared from the commercially available acid by a process which consists of preparing the hydrochloride salt of the acid and then in reacting it with the alcohol.

It is also known to prepare the 2-hydroxy-4-methylthiobutyric acid esters by hydration of 2-hydroxy-4-methylthiobutyronitrile by sulphuric acid to produce the 2-hydroxy-4-methylthiobutyramide. The amide is then converted to the acid by further hydrolysis. The monomeric form of the acid may then isolated from the mixture of monomers, and oligomers and esterified to produce the ester.

We have found that the esters can be prepared from the nitrile which avoids the preparation of the acid, by utilising the same reaction medium for the hydrolysis step and the esterification step.

Accordingly, the present invention provides a process for the preparation of 2-hydroxy-4-methylthiobutyric acid esters which comprises (a) a first step of, reacting 2-hydroxy-4-methylthiobutyronitrile with sulphuric acid to produce 2-hydroxy-4-methylthiobutyramide, and (b) a second step of reacting the 2-hydroxy-4-methylthiobutyramide with an alcohol to produce a 2-hydroxy-4-methylthiobutyric acid esters, the two steps being carried out in the same reaction medium.

The present invention provides the advantage over the known prior art processes in that the ester can be prepared from the nitrile and amide, thus avoiding the preparation of the acid, the chlorination and the subsequent esterification steps as required in the prior art processes. In particular, the process of the present invention provides the advantage over the prior art by avoiding the preparation of the acid and thus the necessary separation step of the monomers from the oligomers is also avoided.

In general, the reaction medium of the two steps comprises sulphuric acid.

The first step of the process is the hydration of 2-hydroxy-4-methylthiobutyronitrile by the addition of sulphuric acid. It has been found that it is possible to carry out the hydration of 2-hydroxy-4-methylthiobutyronitrile to 2-hydroxy-4-methylthiobutyric acid ester with excellent yields when the process is carried out in a highly concentrated sulphuric acid medium and in the presence of a sufficient quantity of water to carry out this reaction. Suitably, the molar ratio of sulphuric acid to 2-hydroxy-4-methylthiobutyronitrile is from 0.6 to 1.2, preferably between 0.6 and 1 and most particularly between 0.6 and 0.88. The rate of the reaction is inversely proportional to the quantity of water. Thus, a quantity of water equal to at least one mole of water per mole of 2-hydroxy-4-methylthiobutyronitrile is necessary. Preferably, the molar quantity of water is from 1 to 3. A molar ratio of water to the 2-hydroxy-4-methylthiobutyronitrile of from 1 to 2.5 is most preferred. Preferably, the 2-hydroxy-4-methylthiobutyronitrile is present in an aqueous solution containing at least 80% 2-hydroxy-4-methylthiobutyronitrile.

This low concentration of water very greatly limits, during the first step, the successive hydrolysis of 2-hydroxy-4-methylthiobutyroamide to 2-hydroxy-4-methylthiobutyric acid. It is thus preferable, during this first step, not to produce more than 5%, preferably less than 2% by weight of 2-hydroxy-4-methylthiobutyric acid. It is also preferable, during this first step, to obtain a concentration of 2-hydroxy-4-methylthiobutyroamide greater than 95% by weight, preferably greater than 98% by weight.

The operating conditions used in the first step are chosen within limits which do not lead to the production of 2-hydroxy-4-methylthiobutyric acid; it is thus preferable to work at a temperature of less than 60° C. and in particular from 0 to 50° C. The reaction pressure is preferably chosen between 0.01 and 3 bar.

The reaction is preferably carried out in a continuous system of reactors in series with a residence time of between 15 minutes and 2 hours.

The second step of the reaction is an esterification and or concomitantly a hydrolysis and an esterification of the 2-hydroxy-4-methylthiobutyroamide to a 2-hydroxy-4-methylthiobutyric acid ester. The second step is carried out in the presence of the remaining quantity of sulphuric acid not consumed in the first step and in the presence of a sufficient quantity of alcohol to esterify the amide present. The molar ratio between the alcohol and the amide is preferably between 2 and 6 and most particularly between 2 and 4. The alcohol is suitably an aliphatic alcohol containing 1 to 10 carbon atoms. The alcohol may be linear or branched. The use of a branched alcohol and most particularly of isopropyl alcohol is preferred.

This second step may be carried out, at a temperature of between 60 and the boiling point of the alcohol and under a pressure of from 0.5 to 5 bar. A pressure below atmospheric pressure makes it possible to remove traces of foul-smelling light gases for example of the dimethyl sulphide, dimethyl disulphide and methyl mercaptan type. The small excess of acid and the presence of ammonium hydrogen sulphate greatly limit the corrosive power of the medium at this temperature.

The process of the present invention may be carried out on a industrial scale and a means of carrying out the invention industrially may be according to the following sequence of steps starting with a concentrated solution of 2-hydroxy-4-methylthiobutyronitrile. A concentrated solution of 2-hydroxy-4-methylthiobutyronitrile and a solution of concentrated sulphuric acid, containing less than 20% by weight of water, is used.

The concentrated 2-hydroxy-4-methylthiobutyronitrile at about 80% by weight and the concentrated sulphuric acid at about 90% by weight are fed to an apparatus in which the 2-hydroxy-4-methylthiobutyronitrile is hydrated. A solution containing 2-hydroxy-4-methylthiobutyramide and any unreacted sulphuric acid is thus obtained. The alcohol is added to this solution. The solution obtained after heating contains the 2-hydroxy-4-methylthiobutyric acid ester. The 2-hydroxy-4-methylthiobutyric acid ester is recovered from this solution.

This particular industrial process may be carried out continuously, semi-continuously or batchwise. When the process is carried out continuously, the apparatus used for the hydration of 2-hydroxy-4-methylthiobutyronitrile may comprise a first stirred reactor with an external recirculation loop which in particular serves to remove the heat released by the reaction. The hydration of the 2-hydroxy-4-methylthiobutyronitrile may be completed in one or more stirred or piston reactors, preferably in series with the first reactor. A solution containing 2-hydroxy-4-methylthiobutyramide is thus obtained.

The alcohol is added to the amide solution. The apparatus used for the hydrolysis/esterification or the esterification of the 2-hydroxy-4-methylthiobutyramide may comprise a first stirred reactor. The hydrolysis/esterification or the esterification of the 2-hydroxy-4-methylthiobutyramide may be completed according to a scheme for industrial implementation in one or more stirred or piston reactors in series with the first hydrolysis reactor.

The industrial process may equally be operated starting with concentrated 2-hydroxy-4-methylthiobutyronitrile at about 80% by weight, the alcohol and sulphuric acid. The concentrated 2-hydroxy-4-methylthiobutyronitrile at about 80% by weight, the alcohol and the sulphuric acid are fed under the conditions described in the first process suitable for industrial implementation and the 2-hydroxy-4-methylthiobutyronitrile is hydrated. A solution containing 2-hydroxy-4-methylthiobutyramide, alcohol and a certain quantity of ester is thus obtained. This solution is then heated in order to esterify and/or hydrolyse/esterify the remaining 2-hydroxy-4-methylthiobutyramide. The solution obtained after esterification contains the 2-hydroxy-4-methylthiobutyric acid ester. The 2-hydroxy-4-methylthiobutyric acid ester is recovered from this solution by any suitable means.

It is possible to carry out this process continuously, semicontinuously or batchwise.

According to a third process for industrially operating the invention, the end of the second step is carried out under pressure. The esterification of the 2-hydroxy-4-methylthiobutyramide accelerates when the temperature increases. In order to exceed the boiling point of the medium, this step may be carried out under pressure, for example from atmospheric pressure to 10 bar.

The mixture obtained may then be treated following the hydrolysis step, by a neutralising step followed by a step of two-phase separation and drying each of the two phases followed by for one a filtration step and for the other a crystallisation step. The final titer is adjusted by the addition of water. An equivalent process may be used for the separation of the ester.

A possible treatment process includes carrying out a direct extraction from the hydrolysis medium with a solvent which is immiscible with water followed by evaporation of said solvent in the presence of a quantity of water so as to reduce the appearance of a brown colour of the product obtained. The solvent is chosen from methyl ethyl ketone, methyl isobutyl ketone, methyl tertiary-butyl ether, di-isopropyl ether, diethyl carbonate. An equivalent process may be used for the separation of the ester.

A process comprising phase separation may also be used. A basic neutralising agent of the amine or alkali metal hydroxide type is added to the medium resulting from the esterification step; the use of ammonium hydroxide is preferred. The medium separates into an organic phase containing the desired ester, and remaining salts. The aqueous phase constituting the other phase containing essentially inorganic salts, especially ammonium hydrogen sulfate and traces of ester. The two phases may be evaporated so as to remove the alcohol in order to obtain an organic solution of the 2-hydroxy-4-methylthiobutyric ester containing small quantities of ammonium sulphate which crystallises; the latter is separated by filtration and the 2-hydroxy-4-methylthiobutyric acid ester is recovered and mixed with the organic phase previously obtained. Alternatively, the inorganic salts present in the solution of 2-hydroxy-4-methylthiobutyric acid ester is eliminated by adding an organic solvent which is only slightly miscible with water, such as in particular methyl ethyl ketone, methyl isobutyl ketone, diethyl carbonate or chlorinated solvents. The release of a saline aqueous phase is then observed, the organic phase is freed of the solvent and the residual alcohol by evaporation and the 2-hydroxy-4-methylthiobutyric acid ester is separated.

The aqueous phase is evaporated so as to precipitate the inorganic salts, essentially the ammonium sulphate which may be marketed as it is but which contains traces of foul-smelling organic derivatives. This aqueous phase may also be treated so as to deplete it of 2-hydroxy-4-methylthiobutyric acid ester. This depletion is achieved by addition of a solvent which is only slightly miscible with water chosen from methyl ethyl ketone, methyl isobutyl ketone, diethyl carbonate and chlorinated solvents. The aqueous phase freed of its organic derivatives is dried so as to isolate the odourless inorganic salts which can be marketed directly. The organic phase for depletion is recycled, for example, with the 2-hydro-4-methylthiobutyric acid ester phase in order to recover the quantities of ester which are extracted from the saline aqueous phase.

The present invention will be described with reference to the following examples.

In the following examples, HMTBN is understood to mean the 2-hydroxy-4-methylthiobutyronitrile and HMTBE is understood to mean the 2-hydroxy-4-methylthiobutyric acid ester.

EXAMPLE 1

Synthesis of Isopropyl HMTBE from HMTBN
Preparation of HMTBM:

314.4 g of HMTBN at 78.47% (1.88 mol) was loaded into a jacketed stirred reactor provided with baffles. 201.3 g of 95% sulphuric acid (1.951 mol) was added slowly, while maintaining the temperature below 50° C. After the introduction of the acid was complete, the reactor temperature was maintained at 45° C. for 15 minutes.
Synthesis of isopropyl HMTBE:

At the end of the period for maintaining the temperature, 227.3 g of isopropanol was introduced into the reactor. The reactor is heated in steps of 5°C. per 5 minutes to boiling temperature, 116° C. at the base and 75° C. at the top. The reactor conditions were maintained for 5 hours. Part of the distillate was drawn off and replaced with the same amount of fresh isopropanol.
Neutralisation of the organic phase:

The reaction mass was neutralised with 161.2 g of ammonium hydroxide at 32% (2.72 mol) of ammonia.
Extraction:

Two phases were obtained. 780 g of water and 449.7 g of dichloromethane were added. The neutralised mass was separated after settling out and 939.1 g of organic phase and 1247.4 g of aqueous phase were obtained. Purification:

The light fractions were removed by distillation under low pressure. The distillation was continued by increasing the temperature of the evaporator bath and by reducing the pressure to a few mm of Hg. 263.5 g of distillate was recovered. The isopropyl HMTBE titer is greater than 99%.

The yield of ester was 72% relative to the HMTBN used.

EXAMPLE 2

Synthesis of Isopropyl HMTBE from HMTBN
Preparation of HMTBM:

300.6 g of HMTBN at 80% (1.836 mol) and 228.19 g of isopropyl alcohol were loaded into a jacketed stirred reactor provided with baffles. 192.48 g of 95% sulphuric acid (1.866 mol) was added slowly, whilst maintaining the temperature below 50° C. The acid was added over 37 minutes. After the introduction of the acid was complete, the reactor temperature was maintained at 50° C. for 2 hours 15 minutes.
Synthesis of Isopropyl HMTBE:

At the end of the period for maintaining the temperature, the reactor was heated at boiling temperature (100° C. at the base) for 1 hour.
Neutralisation of the Organic Phase:

200 ml of dichloromethane (261.32 g) and 100 g of water were added to the reactor after cooling. The reaction mass was neutralised to pH 7.7 at 20° C. with 131.24 g of ammonium hydroxide (30%, 2.32 mol of ammonia). An aqueous top phase and organic bottom phase were obtained. 100 ml of water (100.45 g) was added and then the reaction mass was filtered; 305.4 g of cake was recovered.
Extraction:

The reaction mass (1030.4 g) obtained was separated after settling out at 20°C. 701 g of organic bottom phase was obtained; this phase was washed with 245 g of water. 569 g of organic phase was obtained.
Purification:

The light fractions are removed from the organic phase by evaporation under vacuum at 100C. 201.8 g of isopropyl HMTBE was obtained by distillation under reduced pressure whose titer is greater than 99% by weight. The yield is 57% relative to the HMTBN introduced.

EXAMPLE 3

Synthesis of Isobutyl HMTBE from HMTBN
Preparation of HMTBM:

298.34 g of HMTBN at 80% (1.824 mol) and 274.87 g of isobutyl alcohol were loaded into a jacketed stirred reactor provided with baffles. 188.3 g of 95% sulphuric acid (1.825 mol) was added slowly, whilst maintaining the temperature below 45° C. The acid was added over a period of 22 minutes. After the addition of the acid was complete, the reactor temperature was maintained at 50° C. for 10 hours.
Synthesis of Isopropyl HMTBE:

At the end of the period for maintaining the temperature, the reactor was increased to boiling temperature (100° C. at the base). This temperature was maintained for 2 hours. During this time, a solid was formed.
Neutralisation of the Organic Phase:

The reaction mass was neutralised to pH 7.7 at 20° C. with 120.36 g of ammonium hydroxide (30%, 2.12 mol of ammonia). The mixture was filtered and 106.5 g of cake was recovered.
Extraction:

263.8 g of dichloromethane was added to the two-phase filtrate. The two phases were separated by decantation. The aqueous phase was washed with dichloromethane and the organic phase was washed with distilled water. The washings were recycled back to the respective phases. 925 g of organic phase and 250 g of aqueous phase were obtained.
Purification:

The light fractions were removed from the organic phase by evaporation under vacuum at 100° C. 267.8 g of isobutyl HMTBE was obtained by distillation under reduced pressure whose titer is greater than 99% by weight. The yield was 70% relative to the HMTBN introduced.

EXAMPLE 4

Synthesis of Glyceryl HMTBE from HMTBN
Preparation of HMTBM:

299.4 g of HMTBN at 80% (1.826 mol) and 625.6 g of glycerol were loaded into a jacketed stirred reactor provided with baffles. 188.4 g of 95% sulphuric acid (1.826 mol) was added slowly, whilst maintaining the temperature below 50° C. The acid was added over a period of 20 minutes. After the addition of the acid is complete, the reactor temperature was maintained at 50° C. for 12 hours.
Synthesis of Glyceryl HMTBE:

At the end of the period for maintaining the temperature, the reactor temperature was increased in steps to 120° C. The temperature was maintained at 120° C. for 6 hours and then at 130° C. for 1 hour and at 140° C. for 3 hours.
Neutralisation of the Organic Phase:

The reaction mass was neutralised to pH 7.7 at 20° C. with 70g of ammonium hydroxide (30%).
Extraction:

463.8 g of water and 311 g of dichloromethane were added to the neutralised reaction mixture. After decantation, 407 g of organic phase and 1726.3 g of aqueous phase were obtained.
Purification:

The light fractions were removed from the organic phase by evaporation under vacuum at 100°C. 5.8 g of monoglyceryl HMTBE was obtained in the distillation residue.

What is claimed is:

1. A process for the preparation of a 2-hydroxy-4-methylthiobutyric acid ester, which comprises (a) a first step of reacting 2-hydroxy-4-methylthiobutyronitrile with sulphuric acid to produce 2-hydroxy-4-methylthiobutyramide, and (b) a second step of reacting the 2-hydroxy-4-methylthiobutyramide with an alcohol to produce the 2-hydroxy-4-methylthiobutyric acid ester, the two steps being carried out in the same reaction medium.

2. A process as claimed in claim 1, in which the first step is carried out in the presence of a molar quantity of sulphuric acid of from 0.6 to 1.2 relative to the 2-hydroxy-4-methylthiobutyronitrile.

3. A process as claimed in claim 2, in which the first step is carried out in the presence of a molar quantity of sulphuric acid of from 0.6 to 0.8 relative to the 2-hydroxy-4-methylthiobutyronitrile.

4. A process as claimed in claim 1, in which the first step is carried out in the presence of a molar quantity of water of from 1 to 3 relative to the 2-hydroxy-4-methylthiobutyronitrile.

5. A process as claimed in claim 1, in which the 2-hydroxy-4-methylthiobutyronitrile is present as an aqueous solution comprising at least 80% by weight of 2-hydroxy-4-methylthiobutyronitrile.

6. A process as claimed in claim 1, in which the first step is carried out at a temperature of less than or equal to 60° C. and under a pressure of from 0.01 to 3 bar.

7. A process as claimed in claim 1, in which the medium resulting from the first step comprises more than 95% by weight of 2-hydroxy-4-methylthiobutyramide.

8. A process as claimed in claim 1, in which the second step is carried out in the presence of a molar quantity of alcohol of from 2 to 6 relative to the 2-hydroxy-4-methylthiobutyramide.

9. A process as claimed in claim 1, in which the alcohol is a linear or branched aliphatic alcohol having 1 to 10 carbon atoms.

10. A process as claimed in claim 9, in which the alcohol is an aliphatic branched alcohol.

11. A process as claimed in claim 10, in which the alcohol is isopropyl alcohol.

12. A process as claimed in claim 1, in which the alcohol is introduced at the beginning or at the end of the first step.

13. A process as claimed in claim 1, in which the second step is carried out at a temperature of from 60° C. to the boiling of the alcohol and under a pressure of from 0.5 to 5 bar.

* * * * *